(12) United States Patent
Zhang

(10) Patent No.: US 6,897,875 B2
(45) Date of Patent: May 24, 2005

(54) METHODS AND SYSTEM FOR ANALYSIS AND VISUALIZATION OF MULTIDIMENSIONAL DATA

(75) Inventor: Ji Zhang, Rockville, MD (US)

(73) Assignee: The Board of the University of Nebraska, Lincoln, NE (US)

( * ) Notice: Subject to any disclaimer, the term of this patent is extended or adjusted under 35 U.S.C. 154(b) by 128 days.

(21) Appl. No.: 10/057,701

(22) Filed: Jan. 24, 2002

(65) Prior Publication Data
US 2003/0142094 A1 Jul. 31, 2003

(51) Int. Cl.$^7$ ................................................. G07G 5/00
(52) U.S. Cl. ..................... 345/587; 345/586; 345/589; 345/591; 345/597; 382/128; 382/129; 382/225

(58) Field of Search .................................. 345/587, 586, 345/589, 591, 597; 382/128, 129, 225

(56) References Cited

U.S. PATENT DOCUMENTS

| | | | | |
|---|---|---|---|---|
| 5,398,290 A | * | 3/1995 | Brethour | 382/128 |
| 5,544,283 A | * | 8/1996 | Kaufman et al. | 345/424 |
| 2003/0030637 A1 | * | 2/2003 | Grinstein et al | 345/420 |

* cited by examiner

Primary Examiner—Matthew C. Bella
Assistant Examiner—Mike Rahmjoo
(74) Attorney, Agent, or Firm—Welsh & Katz, Ltd.

(57) ABSTRACT

The present invention provides methods and systems to facilitate pattern recognition in complex biological data using component plane presentations of clustered data.

10 Claims, 6 Drawing Sheets

C1  C16  C241  C256

METHODS AND SYSTEM FOR ANALYSIS AND VISUALIZATION OF MULTIDIMENSIONAL DATA

BACKGROUND OF THE INVENTION

The present invention deals with the analysis and visualization of multidimensional data. In particular, the analysis and visualization of multidimensional biological data is addressed.

Biological systems are notorious for their complexity. One small change can have unpredictable consequences in apparently unrelated areas. The study of complex biological systems has a strong reliance upon statistical analysis, and the experience of the analyst in recognizing patterns and designing experiments that highlight the relationships between a multiplicity of factors.

The present invention provides methods and systems for the visualization of complex, multidimensional data in a manner that permits the recognition of a variety of relationships in the data. The present application of a component plane presentation to clustered data from complex biological systems, coloring the clustered data according to values for one component at a time, shows surprisingly different patterns among the clustered data compared to the typical visualization methods of the art, such as U-map and self-organizing map output.

With the completion of human genome sequencing being rapidly approached, functional genomics is becoming extremely prominent in the field of biology. DNA microarray technology emerged [Schena, M., Shalon, D., Davis, R. W., Brown, P. O., "Quantitative monitoring of gene expression patterns with a complementary DNA microarray," *Science*, 270:467–470 (1995)]. In microarray methodology, inserts from tens of thousands of cDNA clones (i.e., probes) robotically arrayed on a glass slide are probed with labeled pools of RNA (i.e., targets). These technological advances have made it possible to conduct research in microscale on very high throughput. Microarray and gene chip technologies permit the parallel conducting of many microreactions on a small scale at one time, using relatively small amounts of reagents. These technological advances in obtaining biological data strengthen the need for simple, visual inspection of the large quantities of data obtained.

Because the amount of data generated by each microarray experiment is substantial—potentially equivalent to that obtained through tens of thousands of individual nucleotide hybridization experiments done in the manner of traditional molecular biology (i.e., Northern blots)—it is extremely challenging to convert such a massive amount of data into meaningful biological networks. Current efforts toward this direction have primarily focused on clustering and visualization methods of data analysis.

The goal of clustering methods is to catalogue genes or RNA samples into functional meaningful groups. Data visualization methods help to exhibit clustering results by conveniently representing the clustered data as an image for visual elucidation.

A commonly applied clustering method is hierarchical clustering, which is an unsupervised clustering algorithm primarily based on the similarity measure between individuals using a pairwise average-linkage clustering [Eisen, M. B., Spellman, P. T., Brown, P. O., Botstein, D., "Cluster analysis and display of genome-wide expression patterns," *Proc. Natl Acad. Sci., USA*, 95:14863–14868 (1998)]. Through the pairwise comparison, this algorithm eventually clusters individuals into a tree view. The length of the branches of the tree depicts the relationship between individuals, where the shorter the branch the more similarity there is between individuals.

A major drawback of hierarchical clustering is the phylogenetic structure of the algorithm. The phylogenetic clustering algorithm may lead to incorrect clustering, which is a particular problem with large and complex data sets, such as those from biological experiments.

Another clustering method that has been gaining in popularity is the recently introduced self-organizing map (SOM) [Kohonen, T., "Self-organizing maps," in Volume 30 of *Springer Series in Information Sciences*, Springer (Berlin, Heidelberg, N.Y.: 1995); Kohonen, T., Oja, E., Simula, O., Visa. A., Kangas, J., "Engineering applications of the self-organizing map," *Proc. IEFE*, 84:1358–1384 (1996)]. SOM is an artificial intelligence algorithm based on unsupervised learning. The SOM algorithm configures the output vectors into a topological presentation of the original data, producing a self-organizing map in which individuals with similar features are mapped to the same map unit or nearby neighboring units. The SOM neighborhood map creates a smooth transition of related individuals to unrelated individuals over the entire map. More importantly, an SOM ordered map provides a convenient platform for visual inspections of large numerical data sets.

SOM has been utilized by several groups for gene clustering analysis [Tamayo, P., Slonim, D., Mesirov, J., Zhu, Q., Kitareewan, S., Dmitrovsky, E., Lander, E. S., Golub, T. R., "Interpreting patterns of gene expression with self-organizing maps: methods and application to hematopoietic differentiation," *Proc. Natl Acad. Sci., USA,* 96:2907–2912 (1999); Toronen, P., Kolehmainen, M., Wong, G., Castren, E., "Analysis of gene expression data using self-organizing maps," *FEBS Lett.,* 451:142–146 (1999); Chen, J. J., Peck, K., Hong, T. M., Yang, S. C., Sher, Y. P., Shih, J. Y., Wu, R., Cheng, J. L., Roffler, S. R., Wu, C. W., Yang, P. C., "Global analysis of gene expression in invasion by a lung cancer model," *Cancer Res.,* 61:5223–30 (2001); White, K. P., Rifkin, S. A., Hurban, P., Hogness, D. S. Microarray analysis of Drosophila development during metamorphosis," *Science,* 286:2179–2184 (1999)].

However, many of the potential benefits of SOM—particularly for visual inspections—have not yet been explored. The deficiency in applying visualization methods to SOM output may have led to the observed under-utilization of the powerful SOM data mining tool in the analysis of microarray data.

The conversion of such massive amounts of data into meaningful information has been limited largely by a lack of robust and easy-to-interpret methods of data analysis. Lately, there have been significant advances in the automation of data organization to facilitate the recognition of characteristic features of a data matrix. The most remarkable advances in data organization revolve around processing the data with a self organizing network to produce a self-organizing feature space mapping. Preferably, the self-organizing network is unsupervised. The organization of the data is known as "training" or "modeling" of the data. However, there remains a need for visualization of the organized data in a manner that facilitates drawing conclusions regarding the data.

Many methods of the art for visualizing data output after data modeling view the value of the final modeled data or reduce the number of dimensions of the data output to a few dimensions (typically two or three dimensions). Examples of visualization methods of the art are shown in FIGS. 2 to 3 and FIGS. 5 to 6, and are discussed in more detail hereinbelow.

Because the present invention involves the visualization of data that has already been clustered, an important aspect of the background of the present invention is the known methods of data clustering. In particular, a brief discussion is warranted of methods of data clustering (organization) known in the art.

One useful statistical method of handling vast quantities of data is to model the data using an independent, iterative process known as SOM (self-organizing map). Although the recently introduced self-organizing map (SOM) has shown promising potentials for the processing of microarray data, the tools utilized to visualize the organized data, to date, fail to fully reveal many beneficial features of the algorithm and depreciate the value of this powerful data mining tool in gene expression analysis.

In "SOM-Based Exploratory Analysis of Gene Expression Data," Samuel Kaski applied SOM technology to the expression of yeast genes, analyzing gene clusters such as genes known to be associated with cytoplasmic degradation, respiration and mitochondrial organization. Kaski visualized the SOM output in a U-matrix (Unified Distance Matrix, a Euclidian neighborhood analysis) display. The SOM was defined by an ordered set of data model vectors, one vector attached to each map unit or grid point.

However, Kaski found the "noisiness" of the U-matrix visualization to be problematic. As a solution, Kaski proposed a method to better define the edges of the clusters by coloring the U-matrix based on the difference between the data gradients of the U-matrix visualized SOM output data cells. Kaski used lightness to show similar data density gradients (i.e. clusters) and color to depict similarity of the data. Kaski's advance in U-matrix visualization of the data provides one approach to better define groups in the clustered data. The present work provides an alternative approach.

In "Analysis and Visualization of Gene Expression Data Using Self-Organizing Maps", by Kaski et al., an SOM-treated nonlinear map of multidimensional genetic data is analyzed and visualized as a hexagonal U-matrix map. Kaski's cluster-defining method discussed above was used in this example application to biological data.

The above methods applied by Kaski at al. focus on analysis of the density of the SOM output model vectors. As such, the methods permit visualization of various aspects of the full SOM output data vector, and the density of the overall data clusters. Kaski's work primarily uses U-matrix visualization of the data and provides one view of possible relationships in the data. There remains a need for additional information to be drawn from the data using alternative visualization methods such as that provided by the present invention (e.g. compare FIG. 1 and FIG. 3).

Another useful statistical method of handling vast quantities of data is to model the data using an independent, iterative process known as feed-forward neural networks. Several patents relating to data organization into clusters include Pao, et al. U.S. Patent Publication No. US 2001/0032198 A1, which is a continuation of U.S. Pat. No. 6,212,509, which is a continuation of U.S. Pat. No. 6,134,537, which is a continuation-in-part of U.S. Pat. No. 5,734,796. Pao et al. use reduced-dimension data mapping of pattern data using conventional single-hidden-layer feed-forward neural networks with nonlinear neurons. Pao et al. visualize the data as a topologically correct low-dimension approximation of the clustered data. Such a visualization method projects the modeled vectors into lower-dimensional space (for example, a sphere may be projected as a circle and a helix as a spiral or zig-zag) and reflects the actual modeled data.

Still another useful statistical method of handling vast quantities of data is to model the data using an independent, iterative process known as hierarchical artificial neural network. Hoffman U.S. Pat. No. 6,278,799 B1 is a continuation of U.S. Pat. No. 6,035,057 disclosing a hierarchical data matrix pattern recognition system that uses a hierarchical artificial neural network for the analysis of complex data to automate the recognition of patterns in data matrices. Hoffman's methodology is applied to weather maps visualized at various altitudes. As with Pao et al., above, Hoffman's visualization method is a projection that preserves the topology of the trained and clustered data.

Almasi et al. teach yet another statistical method of handling vast quantities of data is to model data. Almasi et al. U.S. Pat. No. 6,260,036 B1 discloses a method and apparatus for organizing data into clusters where each cluster comprises a number of records with common input parameters. Almasi et al. visualized the clustered data as a neighborhood map in which the square cells where the data is presented as a dot (relative size depending on the data density) or pie charts in the cells. The visualization method of Almasi et al. is similar to that of Kaski et al., using bar graphs. Such data visualizations, as shown in FIG. 2 are complex and difficult to interpret.

In still another statistical method of handling vast quantities of data, Sirosh U.S. Pat. No. 6,226,408 B1 discloses methods of pre-analysis and clustering of data using unsupervised identification of nonlinear data clusters in multidimensional data. Sirosh visualizes a weighted topological graph of the vector space, using the cluster centers as nodes and weighting the cluster edges between the nodes as a function of the density of the vectors between the linked nodes to depict the relationships between the mapped data. As with Kaski's advance in U-matrix visualization, such visualization methods focus on the density of the clustered data and provide limited means to study the relationships between the clustered data.

Vesanto discloses component plane presentation as a visualization tool of SOM data [Vesanto, J., "SOM-based data visualization methods," Intelligent Data Analysis, 3:111–126 (1999); Basilevsky, A., "Statistical factor analysis and related methods, theory and applications. John Wiley & Sons, New York, N.Y., 1994](9,10). Vesanto fails to teach or suggest the possible potential benefits of the application of component plane presentation visualization methods to draw conclusions about data from biological experiments. None of the other workers who investigated SOM clustering methods on biological data taught or suggested the application of component plane presentation to analyze the data.

As is evident from the discussion above, there are various ways to depict the reduced-dimension data. A common approach is to view a grouped representation of the data vectors. An example of this approach is a map with bar charts in cells representing the data vectors. Bar chart cells near one another depict more closely related data than bar chart cells distant from one another on the map. Similarly, line or pie charts depicting the data can be shown in the cells.

There is a need for other methods and apparati for the visualization of multidimensional data that permits analysis of empirical relationships between the data. Methods of data visualization that permit viewing of the clustered data based on the components of the modeled data, such as the component of time in a time course, temperature of the reaction, intensity of the output, quantity of a reagent, or an empirical parameter, allow appreciation of relationships between the data that may not be apparent from inspection of the full data modeling output.

There is a great demand for easily-interpretable methods and apparati for to visualizing multidimensional data in ways that highlight patterns and trends and/or help data analysts appreciate various aspects of the data.

The present invention provides methods and systems to facilitate pattern recognition in complex biological data using component plane presentations of clustered data.

BRIEF SUMMARY OF THE INVENTION

The present invention provides useful methods and systems for the recognition of patterns and trends in complex multidimensional data using component plane presentations to visualize the data. Typically, the visualization method of the invention begins with data ("individuals") that has already been organized into "map units" representing clusters of strongly similar data. Each cluster represented by a map unit is located on a neighborhood map so that clusters that are more similar to each other are nearer to one another spatially on the neighborhood map. In a component plane presentation of the organized data, the map units of the neighborhood map are shaded according to the values of one of the components of each map unit.

Component plane presentation methods and systems for visualizing multidimensional data are particularly beneficial when applied to complex biological systems, where effects due to changes in various parameters are often quite difficult to predict. Data analysis according to the present invention provides an empirical analysis of the data permitting the visualization of one component of the data at a time in order to ascertain patterns in the organization of the data.

The present invention contemplates a method of visualizing data using component plane presentation comprising the steps that follow. The data is preferably "biological data", the term referring to data from a biological experiment, such as analyses of samples from a variety of patients or a variety of gene sequences. Preferably, the biological data is from a microarray or gene chip, most preferably it is an expression microarray (a microarray providing data regarding gene expression).

A matrix of clustered multidimensional biological data is provided. In the matrix, the rows (or the columns) of the matrix are map units representing clusters of individuals mapped to that map unit, and the corresponding columns (or rows) represent the components of the data cluster. It is understood that a matrix can easily be transformed to interchange rows and columns, so that there is no limitation intended to restrict treatment of a row where treatment of a column can be equivalent.

The clustered biological data is presented as a neighborhood map comprised of the map units, where similar individuals (rows or columns) are mapped to the same or nearby neighboring map units. Such mapping results in the localization of clusters of similar individuals near one another on a topological map. Preferably, the map units are such a geometry that is entirely space-filling, such as squares or hexagons. Hexagonal map units are preferred due to their higher level of symmetry permitting relationships between more neighboring map units.

The map units of the neighborhood map are shaded according to the value of a select component of the data cluster represented by the map unit to provide a component plane presentation to visualize the biological data. Shading has two aspects: color (red, green, blue, yellow, etc.) and hue (brightness, darkness/lightness, or how the various colors would look when converted to black and white picture or gray-scale only). Preferably, a shading scale is defined for each neighborhood map display that shows where each shade falls with regard to color and/or hue and the associated data values. For example, color indices accompany the displays in FIG. 1. Preferably, color is used and not only black and white. The shading of the map units according to the value of the component facilitates the recognition of groups among the clusters of data that are related as far as that particular component is concerned. Preferably, such a component plane presentation is made for each component of the clustered data. The groupings among the data clusters typically varies depending on the component being visualized in any given map.

Typically, data is clustered before being visualized by component plane presentation. The invention contemplates the initial clustering of the data using any of a number of methods of the art, including self-organizing matrix (SOM), feed-forward artificial neural nets and hierarchical neural network methods from artificial intelligence research. Iterative data clustering methods are preferred. In some embodiments, unsupervised data clustering methods are preferred. In other embodiments, supervised data clustering methods are preferred. Self-organizing map clustering methods are particularly preferred.

Thus, in some preferred embodiments, the invention contemplates organizing the multidimensional data involving the steps that follow. An input matrix of data is provided, where the different rows (or columns) i represent different individuals being analyzed (for example in an expression microarray, the rows are the genes) and the different columns (or rows) n represent the outputs of the experiment with variations in a parameter (such as the expression of a given gene at various time points in Example 1, below). The data of the input matrix of biological data is modeled in an unsupervised, iterative manner to produce an output matrix of clustered multidimensional biological data where the rows (or the columns) of the matrix are map units representing clusters of data mapped to that map unit and the corresponding columns (or rows) represent the components of the data cluster. The sequential order of rows (or columns) in the clustered multidimensional biological data implies the position of the map unit on the corresponding neighborhood map.

Typically, the output matrix has a reduced dimensionality as a result of the data clustering. For example, in Example 1, below, various genes are clustered together when their expression at the various time points are similar. The number of rows is the number of map units and the original rows (genes) are mapped into the map units that most closely model their output. The number of columns (components) in the original data and the output matrix are the same.

The invention further contemplates a system for visualizing biological data using component plane presentation. Such a system includes an array data handling means for storing a matrix of clustered multidimensional biological data where the rows (or the columns) of the matrix are map units representing clusters of individuals mapped to that map unit and the corresponding columns (or rows) represent the components of the data cluster. Such a system further includes a visualization means for presenting a topographic neighborhood map comprised of the map units where similar individuals are mapped to the same or nearby neighboring map units. Such a system further includes a shading means for shading the map units of the neighborhood map according to the value of a select component of the data cluster represented by the map unit to provide a component plane presentation to visualize the biological data.

In preferred embodiments, the system further comprises a clustering means for organizing an input matrix of biological data wherein the different rows represent different experiments and the different columns represent the outputs of the experiment with variations in a parameter wherein the input matrix of biological data is modeled in an unsupervised, iterative manner to produce output of a matrix of clustered multidimensional biological data where the rows (or the columns) of the matrix are map units representing clusters of individuals mapped to that map unit and the corresponding columns (or rows) represent the components of the data cluster.

The present invention has many benefits and advantages, several of which are listed below.

One benefit of the invention is that, methods and systems are provided that facilitate pattern recognition in clustered multidimensional data.

One advantage of the invention is that, when applied to biological microarray data, trends in the data stand out that is useful for interpreting complex biological systems.

A further benefit of the invention is that, when applied to microarray data, the methods and systems facilitate the direct determination of the functional significance of the genes regulated in living cells.

An still further advantage of the invention is that, when applied to biologically- or clinically-related samples, the methods and systems of the invention permit the direct correlation of closely related samples.

BRIEF DESCRIPTION OF THE DRAWINGS

In the drawings forming a portion of this disclosure.

DEFINITIONS

Figure 1:
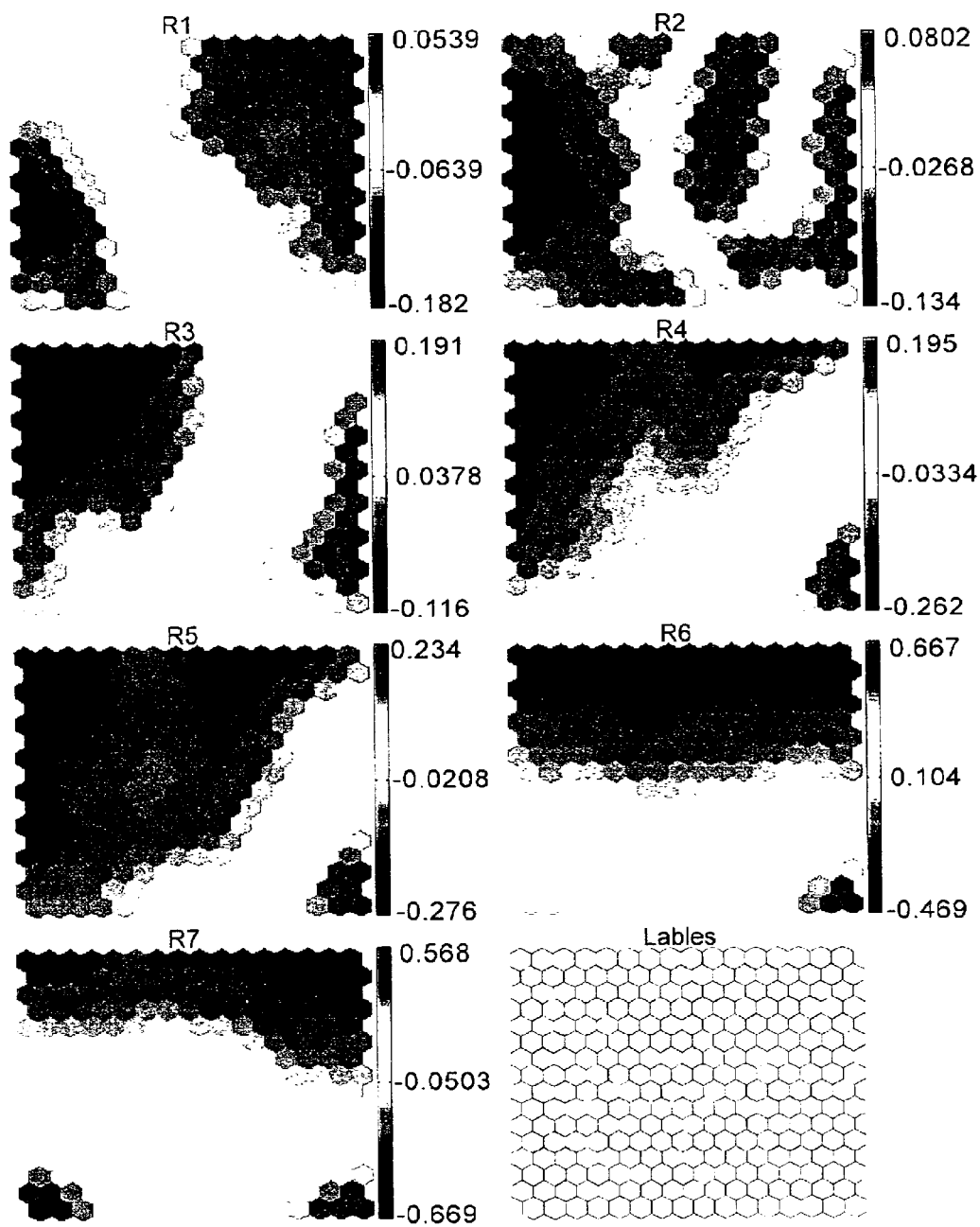
FIG. 1 illustrates a comparison for the same set of data (discussed in Example 1) of a set of component plane presentations. The clusters of yeast genes were organized into 256 (16×16) hexagonal map units. The set of component plane presentations, R1 to R7, illustrate differential displays of regulated genes during the diauxic shift at the genome-wide scale. The color coding index (scale to the right of each of R1 to R7) stands for the expression value range of the component of the genes. These differential displays are linked by position: in each display, the hexagon in a certain position corresponds to the same map unit. It is straightforward to compare expression patterns in same positions of different displays. The last label display shows the position of each unit on the map.

The language used in this disclosure and claims has the meaning as commonly understood in the art. To facilitate understanding of the invention, a number of terms are defined below.

As used herein, "organized data" refers to data that has been modeled, for example using a method of the art, such as self-organizing matrix (SOM) or feed-forward neural net. Herein, the original data before organization is an "input matrix" and the modeled data after organization is an "output matrix". In the language of neural network data modeling, the organization or modeling of the data, from the input matrix to the output matrix, is referred to as "training" the data.

In the present description of the invention, the rows (or columns) of the input matrix are referred to as "individuals" and the rows (or columns) of the output matrix are referred to as "map units".

A "neighborhood map" is a drawing that shows the relationship between data, typically from the output matrix after organization. In a neighborhood map, clusters that are more similar to each other are represented by map units that are nearer to one another spatially.

The term "map unit" refers to a cell on a neighborhood map that represents a modeled data cluster that have been output from the data organization. In the figures herein, the map units are depicted as hexagonal cells, each touching six other neighboring map units. In the examples herein, each row of the SOM output matrix represents a map unit. The physical position of the map unit on the neighborhood map is reflected by the sequential ordering of the rows in the output data.

The term "component" of the data uses the matrix algebra sense of the term, referring to the columns (or rows) of the output matrix. In a typical translation of observations in the real world to a data matrix to describe the observed events, components (typically the matrix columns) often reflect parameters of the data that are being studied, such as time points, temperatures, reagent identities or concentrations.

"Component plane presentation" refers to a presentation of data from a single component of a data matrix at a time. In the context of the present invention, the data from a single component of the output matrix is presented using shading on the neighborhood map.

The terms "microarray" and "gene chip" refer to biotechnological methods and tools typically used for DNA analysis and screening. The "array" and "chip" refer to the arrangement of the samples on the physical experimental surface.

DETAILED DESCRIPTION OF THE INVENTION

The present invention provides useful methods and systems for the recognition of patterns and trends in complex multidimensional data using component plane presentations to visualize the data. Typically, data has been organized into clusters of strongly similar data. Each cluster is represented by a map unit that is located on a neighborhood map so that clusters that are more similar to each other are nearer to one another spatially on the neighborhood map. In a component plane presentation of the organized data, the map units of the neighborhood map are shaded according to the values of one of the components of each map unit.

Component plane presentation methods and systems for visualizing multidimensional data are particularly beneficial when applied to complex biological systems, where effects due to changes in various parameters are often quite difficult to predict. Data analysis according to the present invention provides an empirical analysis of the data permitting the visualization of one component of the data at a time in order to ascertain patterns in the clustering of the data.

A. Sources of the Data

Component plane presentation is useful for the recognition of trends in neighborhood-mapped multidimensional data. Many sources of data may benefit from a component plane presentation analysis. The methods provide particular benefits for the analysis of very complex data, such as data from biological systems.

Data from many kinds of experiments can be presented in a multidimensional array format suitable for analysis and visualization according the present invention. The data is preferably "biological data", the term referring to data from a biological experiment, such as analyses of samples from a variety of patients or a variety of gene sequences. Preferably, the biological data is from a microarray, most preferably it is an expression microarray (a microarray providing data regarding gene expression).

The methods and systems of the invention provide particular insight into the complex data from biological microarray experiments. Such experiments include gene expression data in microarray format, such as the genomics experiments coordinated by the National Human Genome Research Institute and the National Institutes of Health.

In a typical microarray experiment, an RNA sample is labeled with a fluorescence conjugated nucleotide, such as Cye-3 dUTP or Cye-5-dUTP, and these targets are selected to show a contrast between two states of mRNA activity, such as a normal vs. disease cell, a wide type vs. transgenic animal, or a general control vs. a series of study samples. The slide is then excited by appropriate wavelength laser beams to generate two 16-bit TIF images. The pixel number of each spot is proportional to the number of fluorescent molecules and hence permits the quantification of the number of target molecules which have hybridized with the spotted cDNA. The differences in intensities of signal at each of the wavelengths reflect the proportion of molecules from the two different target sources that have hybridized to the same cDNA probe.

As noted in the background section, SOM has been under-utilized as a data mining tool for microarray data due to the limited visualization methods applied to biological data, and microarray data in particular, prior to the present invention.

The component plane presentation approach to visualization correlates samples based on similar patterns in identical positions of the displays, which is particularly fruitful for the transcriptional classification of clinical samples, such as tumors. Applications may include patient screening for known biological markers and clustering of patients, tracking of changes during development or progression of a disease state, and many more.

In addition to the determination of functional significance of regulated genes as shown in Example 1, below, genome-wide differential displays are useful to correlate samples through comparison of patterns in identical positions of the component plane presentation displays, which is particularly useful for clinical sample studies. Using the component plane presentation visualization of SOM output, microarray data sets from prostate cancer and lymphoma cases have also been analyzed. The potential impact of this approach on microarray data analysis is substantial and the approach is robust and easy-to-interpret.

B. Preparation of the Data

Multidimensional data for analysis and visualization by a method of the present invention should be provided in digital array format. Data from multiple experiments can be presented in digital array format, for example by using a matrix row for each of the multiple experiments (equivalently, a matrix columns can be used). Each column represents an aspect of the data.

For example, with a typical biological microarray experiment, such as illustrated in the Examples that follow, each position on the microarray is a different experiment and the output is fluorescence of varying intensity. Data from each position on the microarray can then be recorded in the columns of the row for that position, for example temperature, time, amount of reagent, amount of fluorescence, nature of the reagent (such as biological sequence or marker). Typically, the data is normalized, for example to the controls for background fluorescence.

In contrast to the present invention, hierarchical clustering of gene expression data visualizes the genes in a tree format, showing the relatedness between data sets by their nearness on the tree.

In typical data clustering algorithms, the sequential position of the row (or column) of the data in the output data matrix relates to the position of the individual on the corresponding neighborhood map.

The invention contemplates an extended data matrix that provides notes to the analyst of aspects of the original input matrix that the analyst wishes to track. Such recorded notes typically includes parameters regarding the samples from the experiment, such as the reagents (identity and concentrations) and conditions (temperature, treatments steps), and sample labels. This portion of recorded data regarding the experiment is not submitted to data clustering, it is fixed. After data clustering, the fixed matrix optionally includes a data entry noting the position of the map unit on the neighborhood map of the cluster to which the sample had been mapped.

A matrix of clustered multidimensional biological data is provided. In the matrix, the rows (or the columns) of the matrix are map units representing clusters of individuals mapped to that map unit, and the corresponding columns (or rows) represent the components of the data clustering. It is understood that a matrix can easily be transformed to interchange rows and columns, so that there is no limitation intended to restrict treatment of a row where treatment of a column can be equivalent.

The clustered biological data is presented as a neighborhood map comprised of the map units, where similar individuals are mapped to the same or nearby neighboring map units. Such mapping results in the localization of clusters of similar individuals near one another on a topological map. Preferably, the map units are such a geometry that is entirely space-filling, such as squares or hexagons. Hexagonal map units are preferred due to their higher level of symmetry permitting relationships between more neighboring map units.

The data analysis and visualization methods of the invention contemplate the use of standard data handling techniques to prepare the data for analysis, such as normalization or scaling of the data. Such preparation is an optional step that may be carried out on any apparatus, including computers running data handling programs of the art such as Matlab® (The MathWorks, Natick, Mass.), Microsoft® Excel® (Microsoft Corp. Redmond, Wash.) or Corel® Quattro® Pro (Corel Corp. Ottawa, Canada).

In the handling and interpretation of complicated, multidimensional data, traditional algorithms of handling data typically involve steps to reduce the dimensionality of the data. After data processing, visual inspections are usually performed in a two- or three-dimensional space. Some methods of the art involve projection of the data into a lower dimensional space (for example a three-dimensional sphere is projected to a two-dimensional circle and a three-dimensional helix to a two-dimensional spiral), the output being the projected data vectors. The use of such methods to prepare the data before application of a component plane presentation of the invention is contemplated.

Clustering the data is another useful way of organizing the data. Some methods of data clustering involve the selection of parameters and weighting of the data. Typically, data is clustered before being visualized by component plane presentation. The invention contemplates embodiments of the methods of the invention that also include the clustering steps. The initial clustering of the data using any of a number of methods of the art. Iterative data clustering methods are preferred. Unsupervised data clustering methods are preferred. Self-organizing map clustering methods are particularly preferred.

In preferred embodiments, the system further comprises a clustering means for organizing an input matrix of biological data wherein the different rows represent different experiments and the different columns represent the outputs of the experiment with variations in a parameter wherein the input matrix of biological data is modeled in an unsupervised, iterative manner to produce output of a matrix of clustered multidimensional biological data where the rows (or the columns) of the matrix are map units representing clusters of data mapped to that map unit and the corresponding columns (or rows) represent the components of the data cluster.

In a preferred embodiment, data is clustered using self-organizing map using the "SOM Toolbox for Matlab" from the Helsinki University of Technology Laboratory of Computer and Information Science Neural Networks Research Centre. The SOM Toolbox for MATLAB® 5 implementing the Self-Organizing Map algorithm is presently available at www.cis.hut.fi/projects/somtoolbox/. The Mathworks also provides for MATLAB® "MathWorks Neural Network Toolbox", a "GHSOM Toolbox" (growing hierarchical self-organizing maps toolbox), and an "SOM Toolbox" (for Matlab 5).

In addition to the SOM Toolbox, The Mathworks provides several other data handling tools for MATLAB®: "MathWorks Neural Network Toolbox", a "GHSOM Toolbox" (growing hierarchical self-organizing maps toolbox), General Regression Neural Networks for memory-based feed forward networks, Probabilistic Neural Networks and NNSYSID Toolbox for neural network based identification of nonlinear dynamic systems.

Thus, in some preferred embodiments, the invention contemplates organizing the multidimensional data involving the steps that follow. An input matrix of data is provided, where the different rows (or columns) i represent different experiments and the different columns (or rows) n represent the outputs of the experiment with variations in a parameter.

The size of the neighborhood map is selected, and that determines the number of map units, which is equivalent to the number of clusters the data is to be trained into. The number of clusters is typically the number of rows in the final data clustering output matrix. For example, a neighborhood 8 by 8 map units in a hexagonal grid, which is 64 map units. Whether the initial set of experiments began with expression data for 100 genes or 1000 genes), the data will be clustered into 64 rows. The columns in the original data remain as components in the clustered data. As such, the information contained in the original data is modeled by the data in the map unit, and so is retained in the data clustering output matrix. In Example 1, below, the initial data had a row for each gene monitored in the yeast expression data, 6400; after organization of the data, the number of rows was the number of map units, 256. The number of columns, or components, was equal to the number of time points at which the yeast expression data was monitored, 7.

The data of the input matrix of biological data is modeled in an unsupervised, iterative manner to produce output of a matrix of clustered multidimensional logical data where the rows (or the columns) of the matrix are map units representing clusters of data mapped to that map unit and the corresponding columns (or rows) represent the components of the data cluster.

Self organizing map algorithm. Self-organizing map (SOM) algorithm has properties of both vector quantification and vector projection and consequently configures output prototype vectors into a topological presentation of original multidimensional input numerical data. Usually, an input data set is formatted in a gene expression matrix, in which rows represent genes, columns represent RNA samples, and each cell contains a value featuring the transcriptional level of the particular gene in the particular sample. For instance, the data input matrix of yeast diauxic shift data set, containing numerical values for 6400 genes over seven RNA samples, is formatted as the following:

|      | R1       | R2       | R3       | R4       | R5       | R6       | R7       |
|------|----------|----------|----------|----------|----------|----------|----------|
| 1    | 0.1635   | 0.251    | 0.4005   | −0.1844  | −0.2515  | −1.396   | −1.218   |
| 2    | 0.2388   | 0.2987   | −0.3771  | −0.415   | −0.3401  | −0.4941  | 1.433    |
| 3    | −0.04394 | 0.4005   | 0.4114   | 0.2388   | 0.1635   | −0.1844  | −0.1047  |
| 4    | 0.2016   | 0.4114   | 0.2388   | 0        | −0.304   | −0.5146  | −0.05889 |
| 5    | −0.6666  | −0.1844  | 0        | −0.1844  | −0.304   | 1.475    | 3.644    |
| 6    | −0.5564  | 0        | −0.1203  | −0.05889 | −0.304   | 0.3561   | 0.8875   |
| 7    | 0.01436  | 0.6415   | 0.251    | 0        | −0.08927 | 0.1243   | 0.4957   |
| 8    | 0.04264  | 0.2987   | 0.2016   | 0.04264  | −0.2009  | 0.02857  | −0.1047  |
| 9    | 0.6229   | 0.6415   | 0.9184   | 0.5558   | 0.1635   | 1.287    | 1.475    |
| 10   | −0.1361  | −0.6215  | 0.189    | −0.04394 | −0.3585  | 0.1635   | 0.2987   |
| ...  | ...      | ...      | ...      | ...      | ...      | ...      | ...      |
| 6400 | −0.08927 | 0.02857  | 0.3448   | −0.3219  | −0.3959  | −0.5353  | −0.8625  |

SOM consists of a given number of neurons on an usually two-dimensional grid. Each of these neurons is represented by a multi-dimensional prototype vector. The number of dimensions of prototype vectors is equal to that of dimensions of input vectors (i.e. the number of RNA samples for gene comparison, or the number of genes for sample comparison). The number of input vectors is equal to the number of inputs, e.g. the number of genes in the input matrix. The neurons are connected to adjacent neurons by neighborhood relationship, which dictates the topology, or structure of the map. The prototype vectors are initiated with random numerical values and trained iteratively. Each actual input vector is compared with each prototype vector on the mapping grid. The best matching unit (BMU) is defined when the prototype vector of a neuron gives the smallest Euclidean distance to the input vector. Simultaneously, the topological neighbors around the BMU are stretched towards the training input vector so as to have them updated. The SOM training is usually processed in two phases, a first rough training step and then the fine-tuning.

After iterative training, SOM is eventually formed in the format that individuals with similar properties are mapped to the same map unit or nearby neighboring units, creating a smooth transition of related individuals over the entire map. Data outputs are also formatted in a matrix. For instance, SOM of the yeast diauxic data was performed to cluster genes 256 neurons on a two-dimensional (16×16) grid, the output matrix was organized to contain 256 rows (map units) and seven columns. Each row represents a group of genes, each column represents a sample, and each cell contains a numerical value representing the average transcriptional level of the genes grouped to the corresponding unit over the particular sample. This is illustrated by the following output matrix:

C. Visualization of the Data

Typical visualization of clustered data according to the art is to show the Euclidian distance between data clusters in a reduced dimension space. Typically, this type of visualization is presented as a Euclidian map, or U-map of data clustered into map units. Data presented in U-map form are shown in the figures for Examples 1 and 2 for comparison to the component plane presentation of the present invention. The shading of the map units in a U-map typically show distance to the nearest map units, so that darker-shaded units are more similar data. In this manner, the tightness of the groupings of clustered data are apparent.

Another typical visualization of clustered data according to the art is to show the neighborhood map of clustered data and to provide a representation of an averaged clustered data model in each map unit. Data presented in this form are shown in the figures from Examples 1 and 2 for comparison to the component plane presentation of the present invention, with a bar graph in each map unit. In Example 1, the bar graphs show the up- or down-regulation of the clustered genes for each point of time. Such visualization methods are easier to read than the matrix itself, but they are still very complex and it is difficult to easily recognize and draw conclusions about the data.

The component plane presentation typically utilizes the data as clustered into map units from a data organization step. The map units are shaded according the value of the component being shown in that particular component plane presentation.

The map units of the neighborhood map are shaded according to the value of the select component of the data cluster represented by the map unit to provide a component plane presentation to visualize the biological data.

The shading of the map units according to the value of the component facilitates the recognition of groups among the

|      | R1       | R2       | R3       | R4       | R5       | R6       | R7       |
|------|----------|----------|----------|----------|----------|----------|----------|
| 1    | −0.02023 | −0.18157 | −0.33096 | −0.92365 | −0.97557 | −1.64    | −1.63384 |
| 2    | −0.02134 | −0.15914 | −0.28562 | −0.85213 | −0.8995  | −1.48091 | −1.529   |
| 3    | −0.00724 | −0.10406 | −0.17571 | −0.74599 | −0.78388 | −1.26012 | −1.36246 |
| 4    | 0.021609 | −0.04431 | −0.06552 | −0.67675 | −0.7205  | −1.11426 | −1.25684 |
| 5    | 0.032951 | −0.0273  | −0.05956 | −0.63632 | −0.70399 | −0.9784  | −1.33554 |
| 6    | 0.031634 | −0.06298 | −0.08795 | −0.62434 | −0.69713 | −0.9057  | −1.55557 |
| 7    | 0.051104 | −0.05794 | −0.04642 | −0.64035 | −0.7092  | −1.02828 | −1.72335 |
| 8    | 0.089432 | −0.0132  | 0.012861 | −0.65038 | −0.72701 | −1.31788 | −1.87208 |
| 9    | 0.115188 | 0.012877 | 0.050063 | −0.62827 | −0.70944 | −1.58679 | −2.06228 |
| ...  | ...      | ...      | ...      | ...      | ...      | ...      | ...      |
| 256  | −0.04859 | 0.12509  | 0.443208 | 0.732224 | 0.863023 | 2.46108  | 2.1      | clusters of individuals that are related as far as that particular component is concerned. Shading can be done on a gray-scale, where the value of the average component of the clustered data defines the hue (darkness or lightness) of the map unit. Preferably, shading is in full color. Preferably, a scale showing the relationship between the colors and the values is accessible to the data analyst.

A contemplated system for visualizing biological data using component plane presentation includes an array data handling means for storing a matrix of clustered multidimensional biological data where the rows (or the columns) of the matrix are map units representing clusters of individuals mapped to that map unit and the corresponding columns (or rows) represent the components of the data cluster. Array data handling means may be provided by programs of the art such as Matlab® (The MathWorks, Natick, Mass.), Microsoft® Excel® (Microsoft Corp. Redmond, Wash.) or Corel® Quattro® Pro (Corel Corp. Ottawa, Canada).

A contemplated system for visualizing biological data using component plane presentation includes a visualization means for presenting a topographic neighborhood map comprised of the map units where similar data is mapped to the same or nearby neighboring map units. Such a system further includes a shading means for shading the map units of the neighborhood map according to the value of a select component of the data cluster represented by the map unit to provide a component plane presentation to visualize the biological data. Visualization means including a shading means can be provided by data graphing programs of the art such as Matlab® (The MathWorks, Natick, Mass.), Microsoft® Excel® (Microsoft Corp. Redmond, Wash.) or Corel® Quattro® Pro (Corel Corp. Ottawa, Canada) set up on appropriate computers with appropriate monitors and/or printers.

Preferably, such a component plane presentation is made for each component of the clustered data. The groupings among the data clusters typically varies depending on the component being visualized in any given map. Thus in preferred analysis method of the invention, several component planes are presented, most preferably one for each component of the clustered data.

Component plane presentations of SOM outputs. An SOM data clustering output matrix can be visualized by different ways. When each row is plotted as a curve or a bar graph based on the values in all samples, sequential arrays of all rows into a 16×16 grid, a curve or a bar graph display is formed, illustrating the global view of gene clustering and patterns of expressed genes. Component plane presentations provide a more in-depth approach to visualize variables that contribute to SOM. When all output values of each component (column) are sequentially arrayed into a 16×16 grid, component plane presentations are formed.

Each of component plane presentations is considered as a sliced version of SOM, illustrating values of a single vector component in all map units. For example, in FIG. 1, the first component plane (R1) shows the SOM slice at the time point of 9 hour and last one (R7) shows the SOM at 21 hour during the diauxic shift. The colors of map units are selected so that the color indicates the average expression value of the genes mapped to the corresponding unit (there is a scale to the right of each component plane slice showing the values corresponding to the various colors). Each of these SOM slices can also be considered as a genome-wide differential display of regulated genes, in which all up-regulated units (hexagons in red), down-regulated units (hexagons in blue), and moderately transcribed units (hexagons in green and yellow) are well delineated. By comparing these displays, we can directly determine functional significances of genes regulated during the diauxic shift. For instance, these displays are sequentially correlated each other, depicting the process of metabolic change from fermentation to respiration at the transcriptional level. The sequential inactivation of genes mapped to two upper corners suggests that the functional group represented by genes on the left is more sensitive to the depletion of glucose than the one on the right, although both of them are suppressed toward the end of diauxic shift. The sequential activation of genes mapped to two bottom corners even gives us a more vivid picture of the process leading to ethanol consumption. Genes in the bottom left corner are particularly activated at the end of the shift, indicating that these genes are specifically associated with ethanol metabolism. Whereas, the progressively increased expression of genes in the right corner suggests that these genes are associated not only with ethanol metabolism but also with glucose consumption.

As illustrated above, we are able to directly determine functional significances of genes differentially expressed during the process of yeast metabolic change from fermentation to respiration at the genome-wide scale. To reach similar conclusions by other methods, however, would require a much greater effort. This approach is also applicable to microarray data of other organisms, as indicated by our recent application of component plane presentation integrated SOM to mouse brain samples from ten time points of early embryonic development stages, which allowed us to identify a large number of brain development related genes (Example 2, FIG. 4). In addition to the determination of functional significances of regulated genes, this approach can also be used to correlate samples, based on similar patterns in identical positions of the displays, which is particularly fruitful for clinical sample studies. The potential impact of component plane presentation integrated SOM on microarray data analysis can be substantial and we believe that this approach is robust and easy-to-interpret.

EXAMPLE 1

Genome-Wide Differential Displays of Genes Expressed Differentially During Yeast Diauxic Shift In this Example, component plane presentations permit in-depth visualization of SOM output from microarray data, in which transcriptional changes of the entire set of genes are well delineated for each experimental sample. By integrating features of this component plane presentation with SOM, microarray analyses transcend gene clustering to include, inter alia, differential displays of regulated genes on a genome-wide scale. This algorithm is robust and the visualization is both straight-forward and easy-to-interpret.

A previously analyzed yeast diauxic shift data set provides a model system to demonstrate the benefits of this analytical methodology. By comparing the expression values of 6400 genes from RNA samples collected at seven time points before, during, and after the diauxic shift, we were able to directly determine functional significances of genes differentially expressed during the process of yeast metabolic change from fermentation to respiration at the genome-wide scale. This Example demonstrates the substantial potential impact of this approach on microarray data analysis.

This Example demonstrates the substantial benefits of the use of a component plane presentation visualization in the analysis of microarray data. The distinct advantages of this approach to microarray analysis are highlighted by the analysis of a published microarray data set.

An SOM toolbox built in the Matlab 5 computation environment [Vesanto, J., "Neural Network Tool for Data Mining: SOM Toolbox" in *Proceedings of Symposium on Tool Environments and Development Methods for Intelligent Systems*, Oulun yliopistopaino (Oulu, Finland: 2000), pp: 184–196] was utilized for SOM and its visualizations. The yeast microarray data utilized in this Example of the invention consists of expression values of 6400 genes over RNA samples of seven time points during a diauxic shift [DeRisi, J. L., Iyer, V. R., Brown, P. O., "Exploring the metabolic and genetic control of gene expression on a genomic scale," *Science*, 278:680–686 (1997)].

An expression matrix was constructed from the published data, in which the rows represented the 6400 genes, and the columns represented samples of seven time points at 2-hrs intervals. Each cell of this preliminary input matrix contained a pixel ratio between the correspondent time point and the starting point. The preliminary input data matrix was filtered to eliminate gene rows with erroneous values and with missing values in any of the seven columns, and then the data was scaled by logarithm with base 2. The transformed preliminary input matrix served as the input matrix to initiate and train SOM.

SOM consists of 256 "neurons" (which at the end of SOM "training" are "map units") on a two-dimensional grid. Each of these neurons is represented by a multi-dimensional (seven in this case) prototype vector. The number of dimensions of the prototype vector is equal to the dimension of input vectors, which is the number of components to be used in the component plane presentation. The number of input vectors (rows in the SOM input matrix; also called "individuals" herein) is equal to the number of inputs (the number of genes), while the number of neurons (rows in the SOM output matrix; also called "map units" or "clusters" herein) is equal to the number of map units. The neurons are connected to adjacent neurons by a neighborhood relationship that dictates the topology (or structure) of the map.

The prototype vectors are initiated with random numbers and trained iteratively. Each actual input vector is compared with each prototype vector on the mapping grid based on:

$$\|\vec{x} - \vec{m}_c\| = \min_i \{\|\vec{x} - \vec{m}_i\|\},$$

where $\vec{x}$ stands for the input vector and $m_i$ stands for the output vector. The Best-Matching Unit (BMU) is defined when the prototype vector of a neuron gives the smallest distance to the input vector. Simultaneously, the topological neighbors around the BMU are stretched towards the training input vector so as to have them updated as denoted by:

$$\vec{m}_i(t+1) = \vec{m}_i(t) + \alpha(t)[\vec{x}(t) - \vec{m}_i(t)].$$

The SOM training is usually processed in two phases, a first rough training step and then the fine-tuning [Kohonen, T., "Self-organizing maps," in Volume 30 of *Springer Series in Information Sciences*, Springer (Berlin, Heidelberg, N.Y.: 1995)]. After iterative trainings, SOM is eventually formed in the format where inputs with similar features are mapped to the same map unit or nearby neighboring units, creating a smooth transition of related individuals over the entire map. Different visualizations, including component plane and U-matrix presentations, in this Example were performed using the SOM Toolbox described above.

The yeast diauxic shift data set utilized in this Example was previously analyzed by other groups to demonstrate their clustering methods, including hierarchical clustering and various SOM approaches [Eisen, M. B., Spellman, P. T., Brown, P. O., Botstein, D., "Cluster analysis and display of genome-wide expression patterns," *Proc. Natl Acad. Sci., USA*, 95:14863–14868 (1998); Toronen, P., Kolehmainen, M., Wong, G., Castren, E., "Analysis of gene expression data using self-organizing maps," *FEBS Lett.*, 451:142–146 (1999)].

To topologically maximize the number of neighborhood contacts, we used hexagonal prototype vectors instead of rectangular ones for the SOM training. The data organizing algorithm was conducted using 256 prototype vectors on a two dimensional lattice (16×16 grid).

Figure 2:
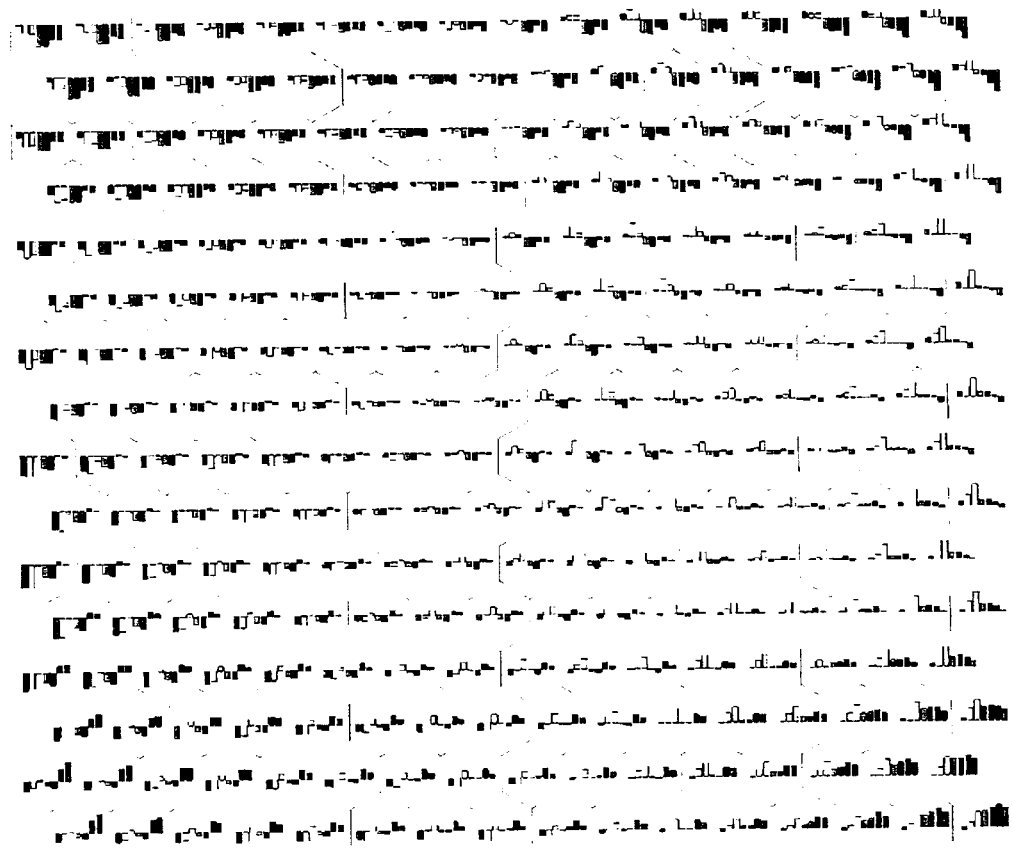
FIG. 2 illustrates the same SOM data shown in FIG. 1 and discussed in Example 1, visualized by a conventional bar-graph display in each map unit. The bar graphic display illustrates gene clustering and expression patterns of regulated genes during the yeast diauxic shift. The bar graph in each unit illustrates the average expression values of genes mapped to the unit. Inserts on the lower panel detail four corner map units: upper left (C1), upper right (C16), bottom left (C241) and bottom right (C256) respectively.
Figure 2:
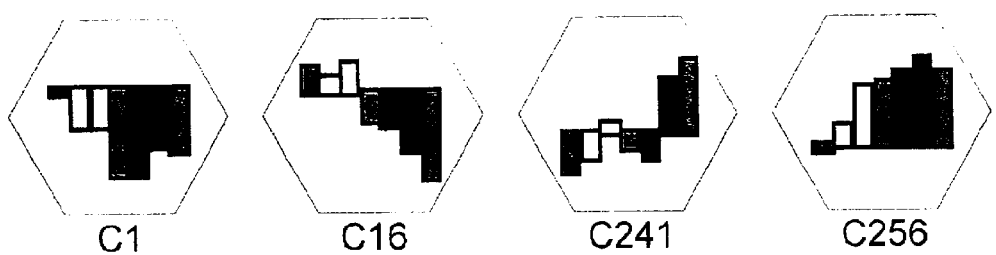

FIG. 2 illustrates a bar-graphical display to visualize the SOM outputs and provides a global view of gene clustering and expression patterns of regulated genes. The bar-graphical display is similar to previously published reports for this same data set [Tamayo, P., Slonim, D., Mesirov, J., Zhu, Q., Kitareewan, S., Dmitrovsky, E., Lander, E. S., Golub, T. R., "Interpreting patterns of gene expression with self-organizing maps: methods and application to hematopoietic differentiation," *Proc. Natl Acad. Sci., USA*, 96:2907–2912 (1999); Toronen, P., Kolehmainen, M., Wong, G., Castren, E., "Analysis of gene expression data using self-organizing maps," *FEBS Lett.*, 451:142–146 (1999); Chen, J. J., Peck, K., Hong, T. M., Yang, S. C., Sher, Y. P., Shih, J. Y., Wu, R., Cheng, J. L., Roffler, S. R., Wu, C. W., Yang, P. C., "Global analysis of gene expression in invasion by a lung cancer model," *Cancer Res.*, 61:5223–30 (2001); White, K. P., Rifkin, S. A., Hurban, P., Hogness, D. S., "Microarray analysis of Drosophila development during metamorphosis," *Science*, 286:2179–2184 (1999)].

The number of genes mapped to individual map units varied between 5 to 89 and the bar chart displayed in each hexagonal unit represented the average expression pattern of genes mapped in the unit. The map has been organized in such a way that related patterns are placed in nearby neighboring map units, producing a smooth transition of patterns over the entire map. A gene cluster can also be recognized from genes represented by closely related neighboring map units in addition to its core unit.

Interestingly, in FIG. 2, genes mapped to edge and particularly corner areas appear to be mostly regulated during the diauxic shift. For instance, genes in upper two corners are suppressed toward the end of the shift and those in bottom corners are especially activated. Inserts in the lower panel of FIG. 2 detail patterns of the four corner map units.

Figure 3:
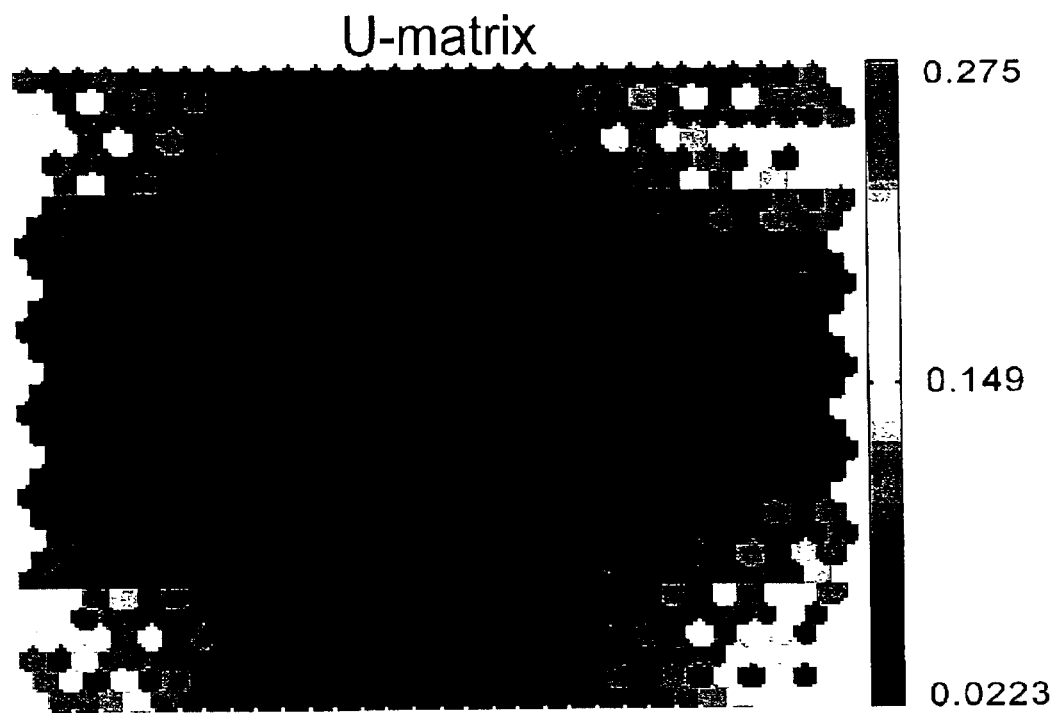
FIG. 3 illustrates the same SOM data shown in FIG. 1 and discussed in Example 1, visualized by a U-matrix presentation to illustrate gene clustering and expression patterns of regulated genes during the yeast diauxic shift. The color coding in U-matrix stands for Euclidean distance between the clustered data in the map units. The darker the color, the smaller the distance between map units and thus the tighter the cluster. The large dark-blue area occupying the greatest portion of the display represents the large number of un-regulated genes, that are not easily distinguishable from one another and are noise clusters.

FIG. 3 illustrates a U-matrix display, a distance matrix method that visualizes the pairwise distance between neighboring map units and helps to define the cluster structure of the SOM output. The large dark-blue area in the central part of the display may correspond to those randomly clustered genes [Toronen, P., Kolehmainen, M., Wong, G., Castren, E., "Analysis of gene expression data using self-organizing maps," *FEBS Lett.*, 451:142–146 (1999)].

FIG. 1 shows the component plane presentation, which illustrates features other than clustering of regulated genes during the diauxic shift. The component plane presentation provides a more in-depth approach to visualize variables that contribute to the clustering in the SOM output. Each of the component plane presentations, R1 to R7, is a sliced version of SOM, illustrating values of a single vector component in all map units.

For example, the first component plane (R1) in FIG. 1 shows the SOM slice at the time point of 9 hours and last one (R7) shows the SOM at 21 hours during the diauxic shift. The colors of map units are selected so that more vivid the color, the greater the average expression value of the genes mapped to the corresponding unit. A scale showing the correspondence between expression value and color accompanies the presentation. Each of these SOM slices can also be considered as a genome-wide differential display of regulated genes, in which all up-regulated units (hexagons in red), down-regulated units (hexagons in blue), and moderately transcribed units (hexagons in green and yellow) are well-delineated. By comparing these genome-wide differential displays, we can learn many additional features of regulated genes in cells.

For instance, these displays are sequentially correlated each other, depicting the process of metabolic change from fermentation to respiration at the transcriptional level. As the component plane presentations from R1 to R7 are compared, the sequential inactivation of genes mapped to two upper corners suggests that the functional group represented by genes in the left corner is more sensitive to the depletion of glucose than the one on the right, although both of them are suppressed toward the end of the diauxic shift. The sequential activation of genes mapped to two bottom corners even gives us a more vivid picture of the process leading to ethanol consumption. Genes in the bottom left corner are strongly activated at the end of the shift, indicating that these genes are specifically associated with ethanol metabolism. Whereas the progressively increasing expression level of genes in the right corner suggests that these genes are associated not only with ethanol metabolism, but also with glucose consumption.

These changes, evident from the component plane presentation visualization, are confirmed by known genes mapped to these corner map units. It is clearly shown that genes represented by the upper two corner units (C1 and C16) are mostly related to cell growth and protein synthesis. In particular, genes grouped in map unit C16 are almost exclusively ribosome encoding genes. In addition, many protein synthesis-related genes are found in neighboring map units. Whereas genes in the bottom-left corner are specifically involved in ethanol metabolism, including glyoxylate cycle. Genes in the bottom right corner are involved in glucose metabolism, including TCA (tricarboxylic acid) cycle, in addition to some stress-activated heat shock protein and cytochrome c-related genes. Of course, glucose pathways and TCA cycle are also utilized during ethanol metabolism.

The conclusions draw from the bar graphical and U-matrix visualizations of this data set correlate well to previous analyses of this data set [Toronen, P., Kolehmainen, M., Wong, G., Castren, E., "Analysis of gene expression data using self-organizing maps," *FEBS Lett.*, 451:142–146 (1999); DeRisi, J. L., Iyer, V. R., Brown, P. O., "Exploring the metabolic and genetic control of gene expression on a genomic scale," *Science*, 278:680–686 (1997)].

The self-organizing map, an artificial intelligent algorithm based on unsupervised learning, provides particular insight into microarray data analysis. This algorithm has properties of both vector quantification and vector projection and consequently configures output prototype vectors into a topological presentation of original multidimensional input numerical data. It produces a usually two-dimensional SOM in which individuals with similar features are mapped to the same map unit or nearby neighboring units, creating a smooth transition of related individuals over the entire map. More importantly, this ordered map provides a convenient platform for various inspections of the numerical data set.

To date, visualization methods utilized in the microarray field are primarily focused on gene clustering, typically represented by curve or bar-graphical displays (FIG. 2). U-matrix (unified distance matrix; FIG. 3) is a distance matrix method that visualizes the pairwise distance between prototype vectors of neighboring map units and helps to define the cluster structure of SOM. Methods of the art were used to define some core clusters of developmentally-related genes expressed during brain development. However, the interpretation of the visualization methods of the art are difficult when noise interruption is high, as demonstrated in this Example, where there is a large number of unregulated genes in the diauxic shift data set. The unregulated genes form clusters in a random manner, producing a large noise clustering area in the center of SOM (FIGS. 2 and 3), as also revealed by Sammon's mapping algorithm [Toronen, P., Kolehmainen, M., Wong, G., Castren, E., "Analysis of gene expression data using self-organizing maps," *FEBS Lett.*, 451:142–146 (1999)].

This Example demonstrates how component plane presentations provide a more in-depth approach to visualization of component variables that contribute to SOM and therefore permit slicing of the SOM output into multiple, sample-specific, genome-wide differential displays. Each of these displays details transcriptional changes of a specific sample at the genome-wide scale. These genome-wide differential displays provide distinct advantages in visual inspections for the understanding of biological meaning of microarray data.

As illustrated in this Example, functional significance of genes differentially expressed during the process of yeast metabolic change from fermentation to respiration at the genome-wide scale could be observed. To reach similar conclusions using methods of the art would require a much greater effort [DeRisi, J. L., Iyer, V. R., Brown, P. O., "Exploring the metabolic and genetic control of gene expression on a genomic scale," *Science*, 278:680–686 (1997)].

The component plane presentation visualization approach is also applicable to microarray data of other organisms, as demonstrated in the following Example, applying the approach to microarray data of mouse brain samples from ten time points of early development stages, permitting identification of a large number of brain development related genes.

EXAMPLE 2

Genome-Wide Differential Displays of Genes Regulated During Early Brain Development In this example, murine neural cell expression microarray data was arranged as a data matrix, subjected to some basic transformations, clustered using a self-organizing map algorithm and visualized using component plane presentation visualization, bar graph format, and U-matrix display for the self-organizing map output.

In brief summary, this Example describes high density in silico cDNA microarrays containing 4,608 mouse gene sequences. Mouse brain samples were profiled from ten time points throughout the embryonic brain development. The self-organizing map-based component plane presentation approach permitted visualization of microarray data of each sample in a genome-wide differential display, in which all up-regulated, moderately regulated and down-regulated gene clusters were well delineated.

The component plane presentation visualization of the data facilitated the direct determination of the functional significance of genes regulated at each development stage. A comparison of different displays showed that about 24% of genes regulated during the development were actively transcribed during the early stages, and thus correlated with the fast proliferation of neuroepithelium, the primary proliferative matrix in early brain structures. Functional implications of these genes were associated with virtually every aspect of cell proliferation, including chromosome replication and segregation, cell cycle control system, transcriptional regulation, signal transduction, RNA and protein synthesis, metabolism, mitochondria and other cellular elements. Additionally, a number of apoptosis-related genes were also grouped in this cell proliferation gene cluster, suggesting their involvement in fast segmentation of brain structures during the early development.

The component plane presentation integrated self-organizing map allows microarray data analyses go beyond gene clustering to include genome-wide differential displays of regulated genes at all time points studied and permits the direct determination of functional significances of clustered genes. This Example demonstrates the benefits of the component plane presentation approach to exploration of the molecular networks of mammalian cells in vivo for proliferation, differentiation and fate commitment.

The neuroepithelium is a heterogeneous cell population derived from the neuroectoderm of the neural plate and, serves as the ultimate source of all neural elements of the brain and spinal cord. It is also the major source of neural stem cells. This undifferentiated neural epithelium almost exclusively constitutes the entire brain structures at early stages of embryonic development, and proliferates many times before these cells differentiate into neuronal precursors and other neural elements. Although cytological studies of neuroepithelium have been well documented, little is known about molecular mechanisms involved in the cell proliferation and differentiation. The present Example groups genes regulated during the various stages of murine brain development.

It is apparent that neuroepithelium plays an important role during early brain development. The undifferentiated neural epithelium, derived from the neuroectoderm of the neural plate, serves as the ultimate source of neurons and other neural elements in brain and spinal cord [Altman J., Bayer S. A., *Atlas of prenatal rat brain development*, CRC Press, Inc. (Boca Raton, Ann Arbor, London, Tokyo: 1995); Martinez S., Puelles L., "Neurogenetic compartments of the mouse diencephalons and some characteristic gene expression patterns," in *Mouse Brain Development*,. Goffinet A. M., Rakic P. (Eds), Volume 30 in the series *Results and problems in cell differentiation* Springer-Verlag (Berlin, Heidelberg: 2000) pp:91–106; Marin F., Puelles L., "Patterning of the embryonic avian midbrain after experimental inversions: a polarizing activity from the isthmus," *Dev. Biol.*, 163(1):19–37 (1994)].

In order to understand the molecular mechanisms involved in cell proliferation and differentiation for this tissue type, high-density cDNA microarrays containing 4,608 mouse gene sequences were constructed. These arrays were used to profile mouse embryonic brain samples from embryonic day 9.5 (E9.5) to embryonic day 18.5 (E18.5) at 24 hour intervals.

Mouse sequence verified IMAGE clones were purchased from Research Genetics. To generate gene-specific sequences corresponding to each clone, vector-specific primers were used to direct recover inserts from individual bacterial clones by PCR. Each PCR reaction was examined by gel electrophoresis to ensure good quality as well as a sufficient yield of PCR products. After an ethanol-based precipitation, the insert DNA from each clone was resuspended in a SSC solution and spotted onto poly-L-lysine coated glass slides by a GMS417 arrayer (Affymetrix) with a density of 4,608 spots per 18×18 $mm^2$. These arrays were then subjected to denaturation and hybridization with fluorescent labeled probes.

Normal pregnant mice were sacrificed and all the embryos from the same pregnant mouse were pooled. Normally, eight to ten embryonic brains were dissected from each pregnancy and pooled for total RNA exaction. A modified procedure combining Trizo Reagents (BRL-Gibco) and RNAeasy (Quigen) was used to extract total RNA from the dissected neural tissues. A reverse transcription procedure was utilized to incorporate Cy3-dUTP or Cy5-dUTP into cDNA products.

To minimize variables potential associated with Cy-5 incorporations, a large amount of mouse embryonic liver DNA control RNA was labeled with Cy-5 and used as a control for all the hybridizations included in this Example. Hybridization was performed in a 3SSC solution containing mouse Cot-1 DNA, polyd(A) and 20 mM HEPES (pH 7) under a coverslip in a moist conical tube overnight at 65° C. Further detailed procedures for array fabrication, probe preparation and hybridization are illustrated at www.unmc.edu/microarray.

The hybridized array was then excited by appropriate wavelength laser beams through a scanner to generate two 16-bit TIF images, which permitted direct measurement of the pixel number of each spot and hence, the relative abundance of the gene in each RNA sample compared with the reference RNA pool.

A GenePix 4000 scanner and its software package (Axon Instruments) were used for data acquisition. An initial expression matrix was constructed [Brazma A., Vilo J., "Gene expression data analysis," *FEBS Lett.*, 480:17–24 (2000)], in which the rows represented the 4,608 genes, and the columns represented the 10 RNA samples (ED9.5 through ED18.5). Each cell of the expression matrix contained a ratio (Cy-3 vs. Cy-5), as the measurement for relative expression level of each gene across all the samples. Fluorescent ratios (ratio of mean) were calibrated independently for each hybridization by applying a correction factor to all ratios from the same array. This correction factor was computed so that the ratio of well-measured spots on each array was 1.0.

This expression matrix was further filtered to eliminate genes with erroneous values and with missing values in any of the ten samples before scaled by logarithm with base 2 and normalized to norm 0 and variance 1 in order to eliminate the influence from the non-related liver reference and potential data biases [Eisen M. B., Spellman P. T., Brown P. O., Botstein D., "Cluster analysis and display of genome-wide expression patterns," *Proc. Natl. Acad. Sci., USA*, 95(25):14863-14868 (1998)]. The adapted matrix containing values of 2,124 genes from RNA samples at ten time points were further normalized to norm 0 and variance 1 using the function of zscore from Statistic Toolbox of Matlab.

This transformed expression matrix served as the data input matrix format for the statistical analysis. Self-organizing map (SOM) was applied to cluster genes into functional meaningful groups. An SOM toolbox built in Matlab 5 computation environment [Vesanto J., "Neural Network Tool for Data Mining: SOM Toolbox," *Proceedings of Symposium on Tool Environments and Development*

*Methods for Intelligent Systems* 2000, Oulun yliopistopaino, Oulu, Finland, pp:184–196], was utilized to perform SOM algorithms, U-matrix display and component presentations.

Figure 5:
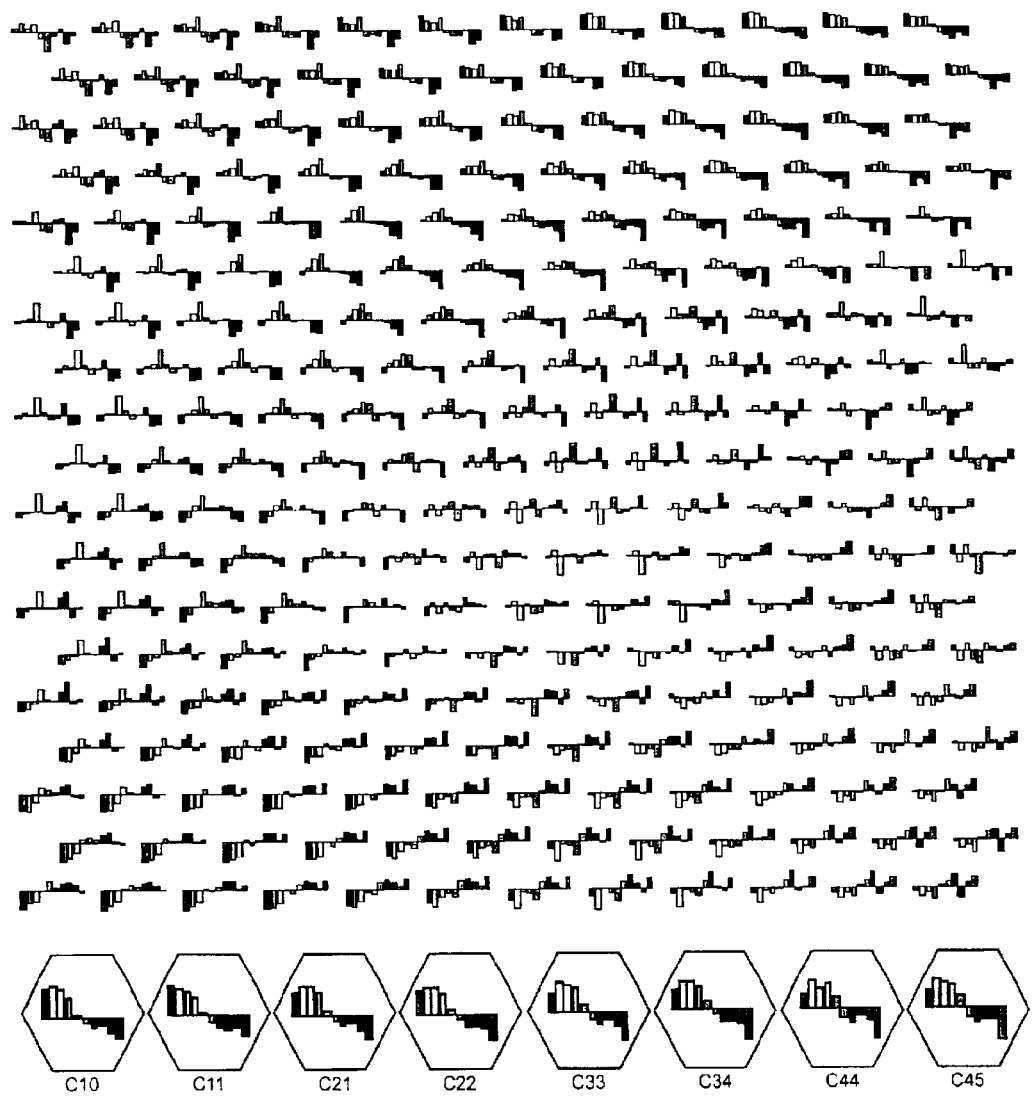
FIG. 5 illustrates a traditional visualization of the self-organizing map (SOM) of gene expression data from mouse prenatal brain development, discussed in Example 2. The bar graphic display illustrates the clustering of 2,124 genes (with a 100% filtering) into 228 (12×19) hexagonal map units. The bar graph in each unit illustrates the average expression values of the genes in the unit versus the time series. Inserts in the right panel illustrate detailed patterns of the values of representative map units in the neuroepithelium proliferation cluster.

Outputs of the SOM are shown in bar graphical display in FIG. 5, which provides a global view of gene clustering and patterns of expressed genes. The number of genes mapped to individual map units varied between 56 to 157.The bar chart displayed in each hexagonal unit represents the average expression pattern of genes mapped in the unit. The map has been organized in such a way that related patterns are placed in nearby neighboring map units, producing a smooth transition of patterns over the entire map. Therefore, a gene cluster can also be recognized from genes represented by closely related neighboring map units in addition to its core unit. Inserts in the lower panel of FIG. 5 detail expression patterns of some representative map units.

Figure 6:
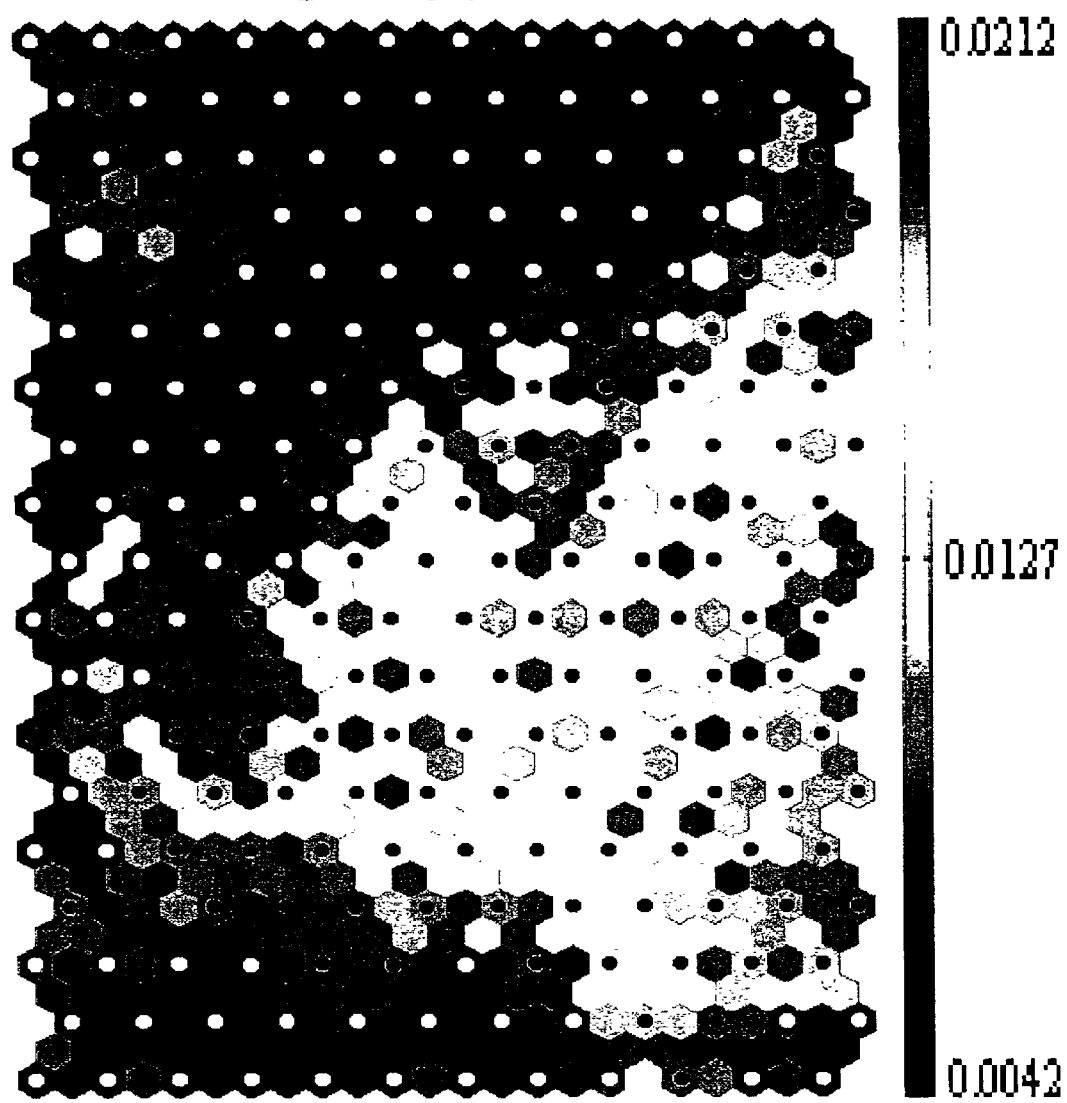
FIG. 6 illustrates the same gene expression data discussed in Example 2, visualized using a U-matrix presentation. The U-matrix display illustrates the cluster structure of the entire SOM. The white or black dots indicate locations of map units, and the hexagons between the dots show the actual values of the U-matrix. The bar code on the right denotes the Euclidean distance. The darker the color, the smaller the distance.

Visualization of outputs of the SOM by U-matrix (unified distance matrix) display (FIG. 6) and component plane presentations (FIG. 4) reveal more detailed features of this clustering. U-matrix is a distance matrix method that visualizes the pair wise distance between neighboring map units and helps to define the cluster structure of SOM. As shown in FIG. 6, the locations of map units are indicated by black or white dots, and associated values (Euclidean distances) between neighboring map units are denoted using color index coding. The darker the color, the smaller the distance. The U-matrix forms several distinct dark-blue areas. Each of them may represent a cluster of closely related genes that possibly share the same biological function throughout the time course of development. This is further supported by the following component plane presentations.

Figure 4:
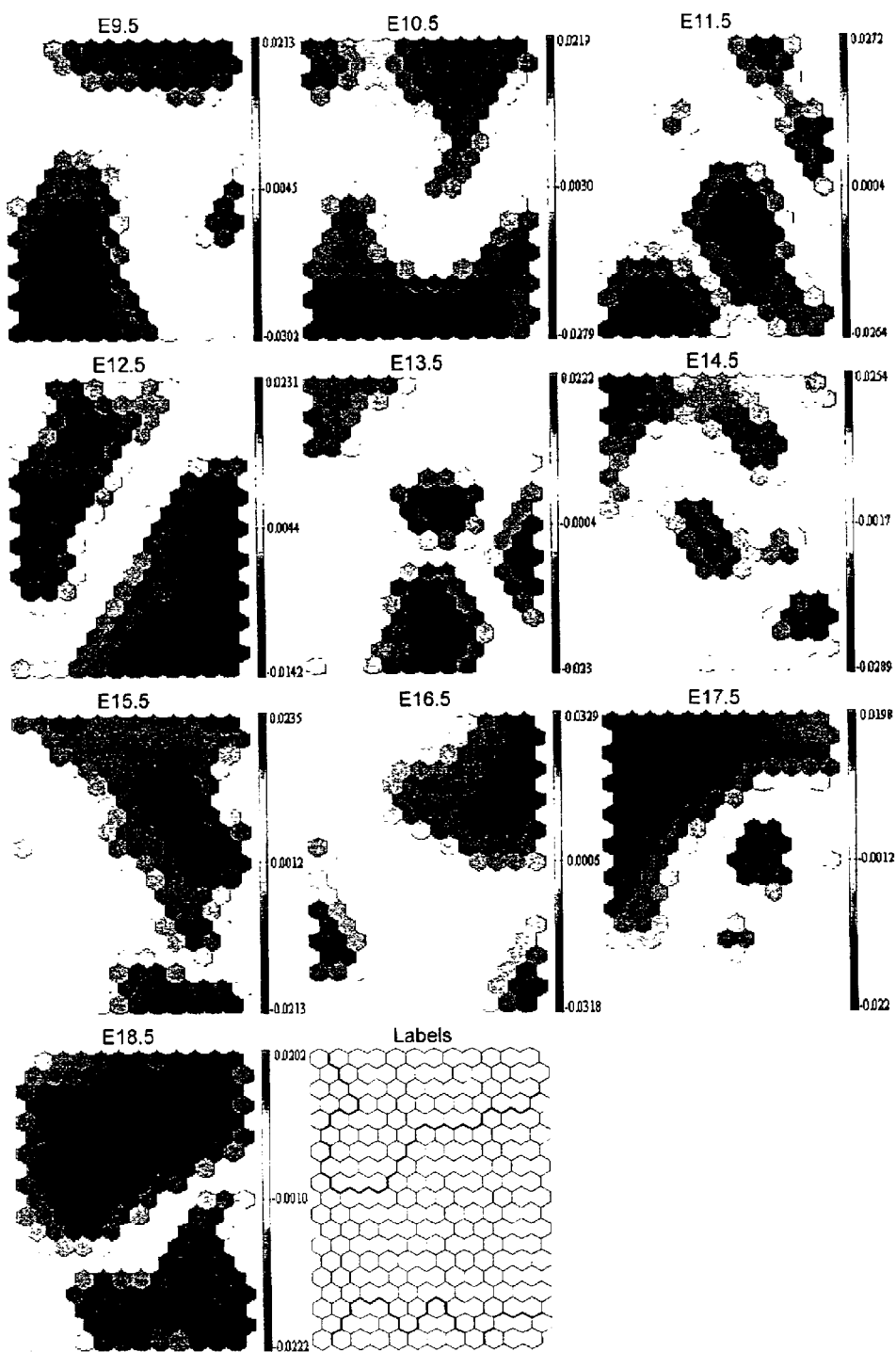
FIG. 4 illustrates self-organizing maps (SOMs) of gene expression data from mouse prenatal brain development, as discussed in Example 2. The SOM data is visualized using component plane presentations. In the component plane presentations (E9.5 to E18.5) the bar code on the right indicates expression value. All of the displays in FIGS. 4 and 5 are linked by position: in each display, the hexagon in a certain position corresponds to the same map unit.

As illustrated in FIG. 4, component plane presentations provide a more in-depth approach to visualize variables that contribute to SOM. Each of component planes is considered as a sliced version of SOM, illustrating relative expression values of a single component (embryonic day) in all map units. For example, the first component plane in FIG. 4 shows the SOM slice at the time point of E9.5 and last one shows the SOM at E18.5. The colors of map units are selected so that the more vivid the color, the greater the average expression value of the genes mapped to the corresponding unit. The value is correlated to the color on the scale shown at the right of each display.

Each component plane in this investigation can also be considered as a time-point specific genome-wide differential display, in which all up-regulated units (hexagons in red), down-regulated units (hexagons in blue), and moderately transcribed units (hexagons in green and yellow) are well delineated. This greatly benefits our visual inspections for the determination of functional significance of genes regulated at each development stage. Similar patterns in identical positions of the component planes are correlated by comparing different component planes.

For instance, the first four component planes (E9.5 to E12.5) are obviously correlated with one another based on their similar patterns of transcriptional changes. Specifically, their up-regulated units largely overlap, indicating that genes mapped to the core region of the overlaps may play active roles through the time period (E9.5 to E12.5), which is embryologically characterized by the initial stage of brain vesiculation and development following the period of neural tube closure.

By looking at the labeled figure, we can clearly see that the overlapped core is essentially same as the gene cluster displayed at the top part of the U-matrix in FIG. 6. This gene cluster becomes moderately regulated during the intermediate stage (E13.5 to 16.5) and down regulated during the final stage (E17.5 to E18.5) of mouse embryonic brain development.

Because brain development is initially composed almost exclusively of neuroepithelial cells, it is unquestionable that the up-regulation of genes in this cluster correlates with the proliferation of this tissue type. Although the neuroepithelium is a heterogeneous cell population in which different aggregates of cells are dedicated to produce specialized brain structures and particular cell types [Okabe S., Forsberg-Nilsson K., Spiro A. C., Segal M., McKay R. D., "Development of neuronal precursor cells and functional postmitotic neurons from embryonic stem cells in vitro," *Mech. Dev.*, 59(1):89–102 (1996)], genes grouped in this cluster are most likely corresponding to a common mechanism by which most, if not all, cell types of neuroepithelium proliferate. Name, description and potential functional involvement of known genes and gene homologues from this cluster were considered. These genes are associated with virtually every aspect of cell proliferation. Interestingly, a number of cell apoptosis-associated genes are also grouped in this gene cluster, which may play roles in fast segmentation of brain structures during early stages.

By correlating all the displays including the U-matrix, it is evident that additional clusters at the bottom of the U-matrix are specifically down-regulated in the initial stage of brain development while up-regulated in later stages, indicating that these genes may be involved in neuroepithelial cell differentiation.

As demonstrated in this Example, component plane presentations provide genome-wide differential displays, facilitating the direct determination of functional significances of genes regulated during different stages of mouse embryonic brain development. Through this approach, 564 cDNA sequences, accounting for 24% of total genes regulated during the development, were grouped into the neuroepithelium proliferation cluster. The genes in that cluster that are known are associated with virtually every aspect of cell proliferation, including chromosome replication and segregation, cell cycle control system, transcriptional regulation, signal transduction, RNA and protein synthesis, metabolisms, mitochondria and other cellular elements.

The presence of several of the known genes in a cluster associated with fast proliferation make scientific sense. For example, the proliferation rate of neuroepithelium is characteristically fast during the initial stage of brain development. The duration of each cycle is estimated to be about 8 hours, which is much shorter than the average of standard cell cycles (20 to 24 hrs) occurred during latter stages of the development. It has also been shown that the G1 phase is the only phase of the cycle whose duration is regulated during brain development [Caviness V S, Takahashi T, Nowakowski RS: "Neuronogenesis and early events of neocortical histogenesis" in *Mouse Brain Development*, Goffinet A. M., Rakic P. (Eds)., Volume 30 in the series *Results and problems in cell differentiation*, Springer-Verlag (Berlin Heidelberg: 2000), pp:107–143].

To ensure the faithful duplication of neuroepithelium within a very short time period, the cellular transcription and translation mechanisms must be restricted to those genes coding for proteins constituting the cell types and proteins involved in fast proliferation. This is strongly implicated by the abundance of many specific transcription factors, transcriptional suppressors and histone deacetylases in neuroepithelial cells [Verreault A., Kaufman P. D., Kobayashi R., Stillman B., "Nucleosome assembly by a complex of CAF-1 and acetylated histones H3/H4," *Cell*, 4;87(1):95–104 (1996)]. This is also true for proteins involved in the machineries for synthesis and processing of cellular molecules.

Additionally, fast cell proliferation also requires efficient degradation mechanisms for many proliferation involved proteins. This is supported by the abundance of various ubiquitin-conjugating enzymes and proteasomes. It is also interesting to notice that a number of cell apoptosis related genes are grouped in this cluster as well, which may associate with the faithful segmentation of various brain structures during the initial stage of brain development. These preceding few paragraphs provide only a few examples of some of the conclusions that can be drawn using the powerful visualization tool of the present invention.

Most of our current knowledge about cell proliferation, differentiation and fate commitment comes from lower organisms, such as yeast, *C. elegans* and *Drosophila*. Corresponding studies for mammalian cells are commonly performed in cultured cells, since an intact animal does not provide easy access to detailed observation.

This Example demonstrates the benefits of the component plane presentation approach to exploration of the molecular networks of mammalian cells in vivo for cellular proliferation, differentiation and fate commitment. The conclusions are supported by the identification of a large number of genes corresponding to the rapid proliferation of neuroepithelium during mouse embryonic brain development. The component plane presentation integrated self-organizing map allows microarray data analysis to go beyond gene clustering to include genome-wide differential displays of regulated genes at various time points and permits the direct determination of the functional significance of clustered genes.

The contributions of Yue Teng, Bogdan Wlodarzcyk, Li Xiao, Shannon Engberg, Richard Finnell, and Ji Zhang to this example of the present data visualization invention are gratefully acknowledged. We acknowledge the University Nebraska Medical Center for the additional support for the work drawn upon here in providing this example of the present invention. Additionally, the mouse neurological research was supported in part by grant HD/--S35396B from the National Institute of Environmental Health Sciences and Nebraska Research Initiative Grant to Richard Finnell.

From the foregoing, it will be observed that numerous modifications and variations can be effected without departing from the true spirit and scope of the present invention. It is to be understood that no limitation with respect to the specific examples presented is intended or should be inferred. The disclosure is intended to cover by the appended claims modifications as fall within the scope of the claims.

What is claimed is:

1. A method of visualizing biological data using component plane presentation comprising the following steps:
   (a) providing a matrix of clustered multidimensional biological data where the rows of the matrix are map units representing clusters of individuals mapped to that map unit and the corresponding columns represent the components of the data clustering;
   (b) presenting the clustered biological data as a series of neighborhood maps, each comprised of the map units where similar data is mapped to the same or nearby neighboring map units of the neighborhood map; and
   (c) shading the map units of each of the neighborhood maps according to the value of one of the select components of the data cluster represented by the map unit to provide a component plane presentation to visualize the biological data.

2. The method according to claim 1 wherein the biological data is from a microarray.

3. The method according to claim 2 wherein the microarray provides data regarding gene expression.

4. The method according to claim 1 wherein the map units are shading by color.

5. The method according to claim 1 wherein the multidimensional biological data was clustered using an unsupervised learning method.

6. The method according to claim 1 wherein the multidimensional biological data was clustered using a self-organizing map method.

7. The method according to claim 1 wherein the neighborhood map is comprised of hexagonal map units.

8. A method of visualizing biological data using component plane presentation comprising the following steps:
   (a) providing a matrix of clustered multidimensional biological data where the rows of the matrix are map units representing clusters of individuals mapped to that map unit and the corresponding columns represent the components of the data clustering;
   wherein the multidimensional biological data was clustered using a self-organizing map method, said self-organizing map method comprising the step of organizing the multidimensional biological data using a method comprising the steps of:
      (i) providing an input matrix of biological data wherein the different rows i represent individual experiments and the different columns n represent the output of that experiment for the parameter n; and
      (ii) modeling the data of the input matrix of biological data in an unsupervised, iterative manner to produce output of a matrix of clustered multidimensional biological data where the rows of the matrix are map units representing clusters of individual experiments mapped to that map unit and the corresponding columns represent the components of the data clustering;
   (b) presenting the clustered biological data as a series of neighborhood maps, each comprised of the map units where similar data is mapped to the same or nearby neighboring map units of the neighborhood map; and
   (c) shading the map units of each of the neighborhood maps according to the value of one of the select components of the data cluster represented by the map unit to provide a component plane presentation to visualize the biological data.

9. A system for visualizing biological data using component plane presentation comprising
   (a) an array data handling means for storing a matrix of clustered multidimensional biological data where the rows of the matrix are map units representing clusters of data mapped to that map unit and the corresponding columns represent the components of the data cluster;
   (b) a visualization means for presenting a neighborhood map comprised of the map units where similar data is mapped to the same or nearby neighboring map units; and
   (c) a shading means for shading the map units of the neighborhood map according to the value of a select component of the data cluster represented by the map unit to provide a component plane presentation to visualize the biological data.

10. A system for visualizing biological data using component plane presentation comprising:
   (a) an array data handling means for storing a matrix of clustered multidimensional biological data where the rows of the matrix are map units representing clusters of data mapped to that map unit and the corresponding columns represent the components of the data cluster;
   (b) a visualization means for presenting a neighborhood map comprised of the map units where similar data is mapped to the same or nearby neighboring map units;
   (c) a shading means for shading the map units of the neighborhood map according to the value of a select component of the data cluster represented by the map unit to provide a component plane presentation to visualize the biological data; and
   (d) a clustering means for organizing an input matrix of biological data wherein the different rows represent different experiments and the different columns represent the outputs of the experiment with variations in a parameter wherein the input matrix of biological data is modeled in an unsupervised, iterative manner to produce output of a matrix of clustered multidimensional biological data where the rows of the matrix are map units representing clusters of data mapped to that map unit and the corresponding columns represent the components of the data cluster.

* * * * *